(12) United States Patent
Hsu et al.

(10) Patent No.: US 9,808,016 B2
(45) Date of Patent: Nov. 7, 2017

(54) PESTICIDE COMPOSITION FOR SHORTENING THE VIRUS LETHAL TIME

(71) Applicant: NATIONAL TAIWAN UNIVERSITY, Taipei (TW)

(72) Inventors: Ju-Chun Hsu, Taipei (TW); Hsiang-Chuan Wang, Taipei (TW); Cheng-Jen Shih, Taipei (TW); Shu-Jen Tuan, Taichung (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 0 days.

(21) Appl. No.: 14/730,597

(22) Filed: Jun. 4, 2015

(65) Prior Publication Data

US 2015/0272128 A1   Oct. 1, 2015

Related U.S. Application Data

(63) Continuation-in-part of application No. 13/900,097, filed on May 22, 2013, now abandoned.

(30) Foreign Application Priority Data

May 23, 2012   (TW) .............................. 101118320 A

(51) Int. Cl.
    *A01N 63/00*    (2006.01)
    *A01N 43/56*    (2006.01)

(52) U.S. Cl.
    CPC .................................. *A01N 63/00* (2013.01)

(58) Field of Classification Search
None
See application file for complete search history.

(56) References Cited

U.S. PATENT DOCUMENTS

| 2013/0315873 | A1* | 11/2013 | Hsu | ........................ | A01N 63/00 |
| | | | | | 424/93.6 |
| 2015/0272128 | A1* | 10/2015 | Hsu | ........................ | A01N 63/00 |
| | | | | | 424/93.6 |

FOREIGN PATENT DOCUMENTS

EP            2090170    *  8/2009

OTHER PUBLICATIONS

Derwent abstract of EP2090170 of Aug. 2009 by Bayer CropScience.*
Wang et al. (Journal of Economic Entomology. 2010; 103 (3): 843-848).*
Gilden et al., "Pesticides and Health Risks", J. Obstet. Gynecol. Neonatal. Nurs., Jan.-Feb. 2010,, pp. 103-110, vol. 39(1).
Hofman, et al., "Efficient gene transfer into human hepatocytes by baculovirus vectors", Proc. Natl. Acad. Sci. U S A., Oct. 24, 1995, pp. 10099-10103, vol. 92(22).
Arakawa et al., "Effects of coadministration of chemical insecticides with nucleopolyhedovirus SpltNPV on the dietary intake of the common cutworm *Spodoptera litura* (Lepidoptera: Noctuidae)", Applied Entomology and Zoology. Published online May 25, 2011; 46: 399-405).
Li., "Virulence of a Nucleopolyhedrovirus to Neodiprion abietis (Hymenoptera: Dipionidae)", Journal of Economic Entomology. 2005; 98 (6): 1870-1875.
Wakil et al., "Insecticidal Efficacy of *Azadirachta indica*, Nucleopolyhedrovirus and Chlorantraniliprole Singly or Combined Against Field Populations of *Helicoverpa armigera* Hubner (Lepidoptera:Noctuidae)", Jan.-Mar. 2012; Chilean Journal of Agricultural Research (72) (1): 53-61.
Siddharth Tiwari et al., "Effects of cyantraniliprole, a novel anthranilic diamide insecticide, against Asian citrus psyllid under laboratory and field conditions", Pest Manag Sci 2013, vol. 69, pp. 1066-1072.

* cited by examiner

*Primary Examiner* — Shanon A. Foley
(74) *Attorney, Agent, or Firm* — Hannah M. Tien

(57) ABSTRACT

The present invention provides a method of shortening pesticidal time of the baculovirus to pest, comprising: (1) preparing a pesticide composition; (2) diluting the pesticide composition 100-3000 times; and (3) spraying the diluted pesticide composition on third or older instars in fields; wherein the pesticide composition comprises: (a) a ryanodine receptor insecticide or a diamides insecticide and (b) baculovirus, wherein the concentration of the ryanodine receptor insecticide or the diamides insecticide is 0.01-75% and the concentration of the nucleopolyhedrovirus is $10^7$-$10^{12}$ PIB/ml. The pesticide composition of the present invention can effectively reduce the lethal time to the pest compared to the baculovirus alone, and also can increase the control effect of the pest compared to the same concentration of the insecticide, when applied in field.

9 Claims, 2 Drawing Sheets

PESTICIDE COMPOSITION FOR SHORTENING THE VIRUS LETHAL TIME

CROSS-REFERENCES TO RELATED APPLICATIONS

Figure 1:
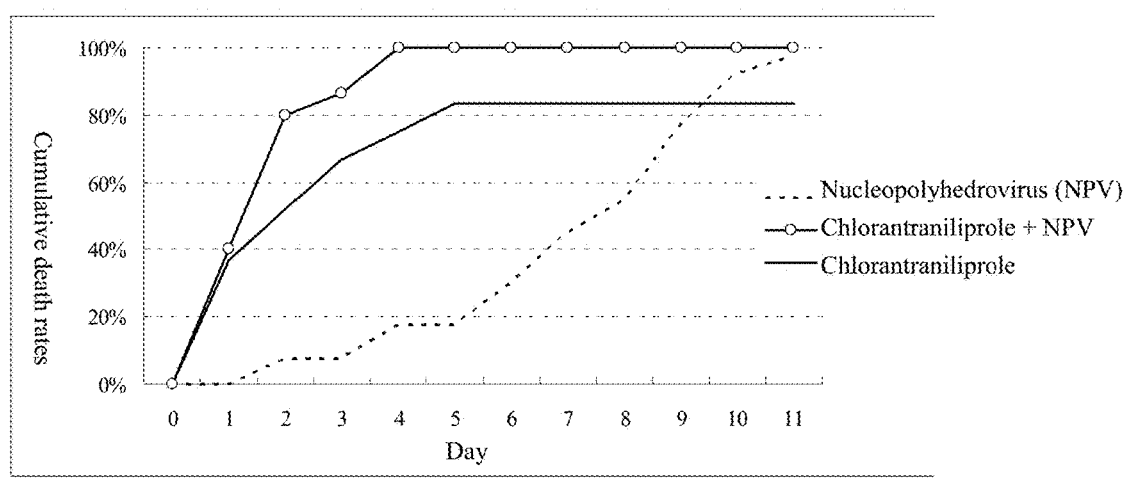

This application is a Continuation-in-Part of co-pending application even on non-target insects. This is especially desirable when beneficial insects are being conserved to aid in an overall Integrated Pest Management (IPM) program, or when an ecologically sensitive area is being treated. The USDA Forest Service currently uses the gypsy moth nuclear polyhedrosis virus (LdNPV) to aerially spray thousands of acres of forest each year. This product, registered as GYPCHEK, is effective against gypsy moths but leaves all other animals unharmed.

On the other hand, the high specificity of baculoviruses is also cited as a weakness for agricultural uses, since growers may want one product to use against a variety of pests. Currently, researchers are attempting to use genetic engineering techniques to expand virus host ranges to the desired pest species. Releases of such genetically-engineered baculoviruses have been made by researchers in the U.K. and the United States and show promise, although the cost of commercial production of these agents must be reduced if they are to be competitive. Companies like Dupont, biosys, American Cyanamid, and Agrivirion have continued to explore the expansion and development of agricultural-use viral insecticides.

Ryanodine and ryanodol are poisonous alkaloids found in the South American plant *Ryania speciosa* (Flacourtiaceae). They were originally used as insecticides. The compounds have extremely high affinity to the open-form ryanodine receptor, a group of calcium channels found in skeletal and heart muscle cells. They bind with such high affinity to the receptor that they were used as labels for the first purification of that class of ion channels and gave its name to it.

At nanomolar concentrations, ryanodine locks the receptor in a half-open state, whereas it fully closes them at micromolar concentration. The effect of the nanomolar-level binding is that ryanodine causes release of calcium from calcium stores in the sarcoplasmic reticulum leading to massive muscular contractions. This is true for both mammals and insects.

Ryanodine receptor modulators are a new kind of synthetic pesticide, which is effective to Lepidoptera pests including the European corn borer, sugar cane borer, codling moth, apple borer and gypsy moth. Chlorantraniliprole, flubendiamide and cyantraniliprole have been already registered.

The mixture of pesticides refers to two or more pesticides simultaneously mixed and used at the same time. By reasonably mixing of pesticides, we can expand their targeting scope or control several pests, even increase the efficacy and reduce the side effect such as resistance of the pests or damage to the crop. However, unreasonably mixing of pesticides would reduce the efficacy or produce damages.

The present invention, compared to the prior art, has the following advantages and effects: in the present invention, low concentration of chemical pesticides are mixed with virus. The present invention maintains the biological characteristics of the virus. Because of the concentration of chemical pesticides herein is only 2% of the amount used in the field, the present invention greatly reduces the risk for human and animals exposing to the chemicals, the pesticide residues and shortens the harvest time. The pests do not easily become resistant to the present invention and the present invention maintains long efficacy. The viral pathogenic time can be reduced for more than 2 folds (only two days can reach 50% of death and 3-4 days to 90% of death). The present invention is suitable for crops such as vegetables, soybeans or peanuts and achieves the control effect in the field.

Furthermore, the present invention is verified for its effectiveness in field application. When spray the insecticide in field, the actual amount contacting the larvae is very low. In addition, there are many factors (e.g. rain, wind, temperature) that would affect the toxicity of the chemical insecticide when applied in field. Previous researches were made in laboratory in which the growth environment is different from field environment. Therefore the data or the used concentration retrieved from those researches had low effectiveness when applied in field.

Therefore, the present invention provides a method of shortening pesticidal time, comprising: (1) preparing a pesticide composition; (2) diluting the pesticide composition 100-3000 times; and (3) spraying the diluted pesticide composition on third or older instars in fields; wherein the pesticide composition comprises: (a) a ryanodine receptor insecticide or a diamides insecticide and (b) baculovirus, wherein the concentration of the ryanodine receptor insecticide or the diamides insecticide is 0.01-75% and the concentration of the baculovirus is $10^7$-$10^{12}$ PIB/ml.

The method of present invention has the synergistic effects of the combination of chlorantraniliprole and baculovirus for at least 4 folds, comparing with applying chlorantraniliprole alone.

In the preferred embodiment of the present invention, the dilution of the pesticide composition is 1000-3000 folds.

In the preferred embodiment of the present invention, the concentration of the ryanodine receptor insecticide or the diamides insecticide is 0.1-50% and the concentration of the baculovirus is $10^7$-$10^{11}$ PIB/ml. In the more preferred embodiment of the present invention, the concentration of the ryanodine receptor insecticide or the diamides insecticide is 0.1-40% and the concentration of the baculovirus is $10^7$-$10^{10}$ PIB/ml.

The pesticide composition of the present invention, which controls pests of moths, flies or beetles and shortens pesticidal time of the baculovirus to pest by more than two folds.

The pesticide composition of the present invention, which is sprayed directly, seed-treated, distributed in fields or mixed with baits or other attractant substances (Ex. food attractants, semiochemicals or pheromone) after dilution to achieve pesticidal effects. In the preferred embodiment of the present invention, the dilution is 100-3000 folds.

In a preferred embodiment, the method of the present invention is used to spray the pesticide composition on third instar or order directly in fields.

In the preferred embodiment of the present invention, the concentration of the ryanodine receptor insecticide or the diamides insecticide in the fields is 0.1-100 ppm and the concentration of the baculovirus in the fields is $10^4$-$10^9$ PIB/ml. In the more preferred embodiment of the present invention, the concentration of the ryanodine receptor insecticide or the diamides insecticide in the fields is 0.5-60 ppm and the concentration of the baculovirus in the fields is $10^5$-$10^9$ PIB/ml. In the most preferred embodiment of the present invention, the concentration of the ryanodine receptor insecticide or the diamides insecticide in the fields is 1.2-20 ppm and the concentration of the baculovirus in the fields is $10^5$-$10^8$ PIB/ml.

In the preferred embodiment of the present invention, the ryanodine receptor insecticide is chlorantraniliprole, flubendiamide or cyantraniliprole and the baculovirus is nucleopolyhedrovirus.

In the preferred embodiment of the present invention, the concentration of the ryanodine receptor insecticide or the diamides insecticide is 0.01-20% and the concentration of the baculovirus is $10^7$-$10^{12}$ PIB/ml. In the more preferred embodiment of the present invention, the concentration of the ryanodine receptor insecticide or the diamides insecticide is 0.1-10% and the concentration of the baculovirus is $10^7$-$10^{11}$ PIB/ml. In the most preferred embodiment of the present invention, the concentration of the ryanodine receptor insecticide or the diamides insecticide is 0.1-5% and the concentration of the baculovirus is $10^7$-$10^{10}$ PIB/ml.

EXAMPLES

The examples below are non-limiting and are merely representative of various aspects and features of the present invention.

Formulation
The amount of virus: $10^8$-$10^{12}$ PIB/ml
Diamides pesticides (chlorantraniliprole): 0.01-75%
Other components
The application usage: diluting 1000-3000 folds
The amount of virus: $10^5$-$10^9$ PIB/ml
Diamides pesticides (chlorantraniliprole): 0.05-75 ppm
Other components Example 1

There was no pest control effect when using the low concentrations of the chemical agents of this formulation (for example, 1.47 ppm of Chlorantraniliprole) alone. When treated with 5.5×$10^5$ PIB/ml of the *Spodoptera litura* nucleopolyhedrovirus alone, the 50% lethal time ($LT_{50}$) of the third instar larvae was 9.2 days. But when treated with the formulation of the present invention, 5.5×$10^5$ PIB/ml of the virus and 1.47 ppm of Chlorantraniliprole, the $LT_{50}$ was shortened to 1-2 days and the 90% of lethal time ($LT_{90}$) was achieved by 3-4 days (see Table 1).

TABLE 1

The $LT_{50}$ of *Spodoptera litura* to the nucleopolyhedrovirus and low concentration of common pesticides

| Treatments | $LT_{50}$ (day) | 95% fiducial limits | $LT_{90}$ (day) | 95% fiducial limits |
|---|---|---|---|---|
| nucleopolyhedrovirus (NPV) | 9.2 | 8.6-10.1 | 16.2 | 14.0-20.2 |
| nucleopolyhedrovirus + 16 ppm Chlorfluazuron | 4.5 | 3.9-5.1 | 10.3 | 8.9-13.0 |
| nucleopolyhedrovirus + 1.47 ppm Chlorantraniliprole | 1.7 | 0.4-2.0 | 3.7 | 2.9-6.3 |

The concentration of the nucleopolyhedrovirus (NPV): 5.5 × $10^5$ PIB/ml

Example 2

The mixing of different pesticides caused different effects, such as antagonism or synergism. But even for the synergism, the effects were only up to a maximum of 2 folds (50% of increase), such as the application of the Chlorfluazuron and nucleopolyhedrovirus. Three days after treating with 5.5×$10^5$ PIB/ml of *Spodoptera litura* nucleopolyhedrovirus, the pests did not die. When treated alone with the chemical pesticides such as Chlorfenapyr, Chlorfluazuron, Metaflumizone and Chlorantraniliprole respectively, the 50% lethal concentrations ($LC_{50}$) were 11.8, 7.48, 32.3 and 1.36 ppm (Table 2). If the chemical pesticides were combined with the virus, only Chlorantraniliprole had the synergistic effects of 4 folds (3 folds of increase) and the other agents such as Metaflumizone had the interfered effects.

TABLE 2

$LC_{50}$ of *Spodoptera litura* to the testing pesticides 3 days after the treatment (treating with 5.5 × $10^5$ PIB/ml of nucleopolyhedrovirus did not cause the death of pests)

| Treatments | $LC_{50}$ (ppm) | 95% fiducial limits (ppm) | Increasing rate | synergistic effects (fold) |
|---|---|---|---|---|
| Chlorfenapyr | 11.8 | 8.83-15.4 | | |
| nucleopolyhedrovirus + Chlorfenapyr | 10.0 | 5.86-17.9 | 15% | 1.18 |
| Chlorfluazuron | 7.48 | 5.35-11.0 | | |
| nucleopolyhedrovirus + Chlorfluazuron | 3.07 | 2.18-4.16 | 144% | 2.44 |
| Metaflumizone | 32.3 | 23.9-42.9 | | |
| nucleopolyhedrovirus + Metaflumizone | 44.2 | 34.2-57.5 | −26.9% | 0.73 |
| Chlorantraniliprole | 1.36 | 0.913-2.01 | | |
| nucleopolyhedrovirus + Chlorantraniliprole | 0.333 | 0.174-0.558 | 308% | 4.08 |

Increasing rate: [$LC_{50}$ of insecticide only-$LC_{50}$ of (npv + insecticide)]/ $LC_{50}$ of (npv + insecticide)
synergistic effects: $LC_{50}$ of insecticide only /$LC_{50}$ of (npv + insecticide)

Example 3

Although mixing of proper pesticides can achieve synergistic effects, the mixture with current concentration for field application equals to twice the amount of pesticides used (If the viruses or pesticides are originally used individually, the mixture would be the same concentration used together). This does not achieve the purpose of reducing. The content of Chlorantraniliprole used in the present invention (2% of the current registered concentration, 1.47 ppm) was 50 folds lower than the existing application technique. When mixing with *Spodoptera litura* nucleopolyhedrovirus, the $LT_{50}$ of the third instar larvae was less than 2 days and the $LT_{90}$ was only 3-4 days. There was no pest control effects in the field with this low concentration (1.47 ppm) administered alone. However, when mixing the low concentration of Chlorantraniliprole with the virus, only 2% of the current registered amount of Chlorantraniliprole was mixed with the virus, 85-95% of control rate was achieved (Table 3).

TABLE 3

The control rate of *Spodoptera litura* in *Brassica oleracea* crops by treating with nucleopolyhedrovirus and different pesticides in the field

| Treatment | Control rate (%) | | | | |
|---|---|---|---|---|---|
| | One week after the first treatment | One week after the second treatment | One week after the third treatment | Two weeks after the third treatment | mean |
| Chlorfluazuron | −3.2 | −50.3 | 38.6 | 19.2 | 1.0 |
| Chlorantraniliprole | 31.6 | 22.9 | 77.3 | −5 | 32 |
| nucleopolyhedrovirus | 61.3 | 56.9 | 69.3 | −28.8 | 40 |
| Chlorfluazuron + nucleopolyhedrovirus | 76.8 | 69.3 | 67 | 81.8 | 74 |
| Chlorantraniliprole + nucleopolyhedrovirus | 73.5 | 84.3 | 93.2 | 87.1 | 85 |

The concentration of the *Spodoptera litura* nucleopolyhedrovirus: $10^6$ PIB/mL; Chlorfluazuron was 5 ppm (20% of the current registered concentration); Chlorantraniliprole was 1.47 ppm (2% of the current registered concentration)

Example 4

The cumulative death rates of the third instar larvae of *Spodoptera litura* to 10% of the registered concentration of Chlorantraniliprole (7.36 ppm), nucleopolyhedrovirus ($5.5 \times 10^5$ PIB/ml) and the mixture of 10% of the registered concentration of Chlorantraniliprole+nucleopolyhedrovirus were shown in FIG. 1. It cost 11 days for the treatment of nucleopolyhedrovirus alone to achieve 100% of death rate. For the treatment of Chlorantraniliprole alone, only 80% of death rate was achieved. By mixing of both agents, 100% of death rate was achieved in the fourth day.

Figure 2:
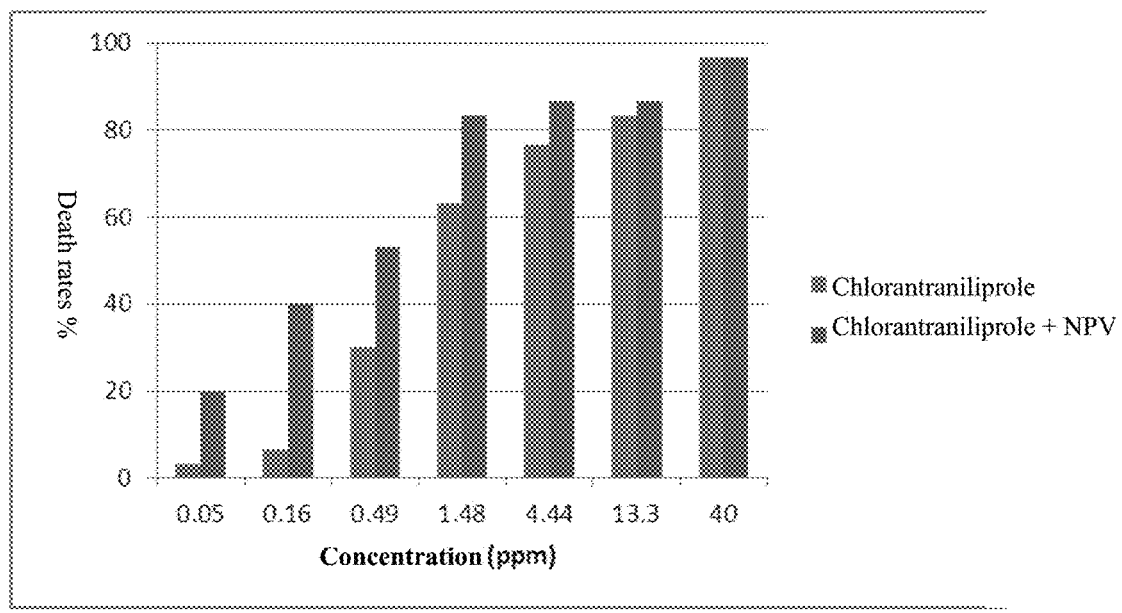

In the indoor experiments, the third instar larvae of *Spodoptera litura* were treated with the mixtures of seven different concentrations of Chlorantraniliprole with the nucleopolyhedrovirus. Except for 40 ppm of Chlorantraniliprole resulting in 100% of death rate can not discriminate the increasing effect of the mixture, from 0.05 to 13.3 ppm, the effects were better for the mixtures than the Chlorantraniliprole alone, showing the increasing effects. The synergistic effect of the mixture was more significant especially in the comparison of the low death rate caused by the low concentration of Chlorantraniliprole (see FIG. 2). The combination of this formulation was evidenced with the scientific experiments to demonstrate non-obvious effects.

What is claimed is:

1. A method of shortening pesticidal time, comprising:
    (1) preparing a pesticide composition, wherein the pesticide composition comprises: (a) a ryanodine receptor insecticide or a diamides insecticide and (b) baculovirus to provide a synergistic effect, wherein the concentration of the ryanodine receptor insecticide or the diamides insecticide is 0.1-2.5% and the concentration of the baculovirus is $5.5 \times 10^8$-$1.65 \times 10^9$ PIB/ml;
    (2) diluting the pesticide composition 1000-3000 times to form a diluted pepticide composition; and
    (3) spraying the diluted pesticide composition on third or older instars in fields.

2. The method of claim 1, wherein the pesticide composition controls pests of moths, flies or beetles.

3. The method of claim 1, which shortens pesticidal time of the baculovirus to pest by more than two folds.

4. The method of claim 1, wherein the ryanodine receptor insecticide is chlorantraniliprole, flubendiamide or cyantraniliprole.

5. The method of claim 1, wherein the baculovirus is nucleopolyhedrovirus.

6. The method of claim 4, wherein the ryanodine receptor insecticide is chlorantraniliprole.

7. The method of claim 5, wherein the ryanodine receptor insecticide is chlorantraniliprole.

8. The method of claim 1, wherein the sprayed concentration of the ryanodine receptor insecticide or diamides insecticide of the diluted pesticide composition in the fields is at least 1.47 ppm and the sprayed concentration of the baculovirus of the diluted pesticide composition in the fields is at least $5.5 \times 10^5$ PIB/ml.

9. The method of claim 1, wherein the sprayed concentration of the ryanodine receptor insecticide or diamides insecticide of the diluted pesticide composition in the fields is 7.36 ppm and the sprayed concentration of baculovirus of the diluted pesticide composition in the fields is at least $5.5 \times 10^5$ PIB/ml.

* * * * *